United States Patent
Zhang

(10) Patent No.: US 10,598,112 B2
(45) Date of Patent: Mar. 24, 2020

(54) METHOD FOR ADAPTING THE CHARACTERISTIC CURVE OF THE NITROGEN OXIDE SENSOR IN AN INTERNAL COMBUSTION ENGINE

(71) Applicant: CONTINENTAL AUTOMOTIVE GmbH, Hannover (DE)

(72) Inventor: Hong Zhang, Tegernheim (DE)

(73) Assignee: Continental Automotive GmbH, Hannover (DE)

( * ) Notice: Subject to any disclaimer, the term of this patent is extended or adjusted under 35 U.S.C. 154(b) by 27 days.

(21) Appl. No.: 16/085,493

(22) PCT Filed: Feb. 2, 2017

(86) PCT No.: PCT/EP2017/052306
§ 371 (c)(1),
(2) Date: Sep. 14, 2018

(87) PCT Pub. No.: WO2017/157568
PCT Pub. Date: Sep. 21, 2017

(65) Prior Publication Data
US 2019/0101075 A1    Apr. 4, 2019

(30) Foreign Application Priority Data
Mar. 16, 2016 (DE) ........................ 10 2016 204 324

(51) Int. Cl.
*F02D 41/14* (2006.01)
*F01N 3/023* (2006.01)
(Continued)

(52) U.S. Cl.
CPC ......... *F02D 41/1461* (2013.01); *F01N 3/021* (2013.01); *F01N 3/023* (2013.01);
(Continued)

(58) Field of Classification Search
CPC ........ F01N 3/021; F01N 3/023; F01N 3/0253; F01N 3/2066; F01N 3/208; F01N 9/00;
(Continued)

(56) References Cited

U.S. PATENT DOCUMENTS

2011/0252767 A1    10/2011  Lin et al.
2015/0276694 A1 *  10/2015  Lahr ........................ F01N 3/208
                                                              73/1.06

FOREIGN PATENT DOCUMENTS

DE    10 2005 011 642    10/2005
DE    10 2008 036 291     3/2009
(Continued)

*Primary Examiner* — Audrey K Bradley
(74) *Attorney, Agent, or Firm* — Cozen O'Connor

(57) ABSTRACT

A method for adapting a characteristic curve of a nitrogen oxide sensor of a combustion engine with exhaust gas recirculation having the first nitrogen oxide sensor upstream of an SCR catalytic converter and a second nitrogen oxide sensor downstream of the SCR catalytic converter includes determining that a particle filter is in a regeneration phase, increasing the exhaust gas recirculation rate, interrupting the supply of urea by a urea injection device, acquiring first nitrogen oxide values from signals generated by the first nitrogen oxide sensor, determining that the first nitrogen oxide values are within a first nitrogen oxide interval, acquiring values from second nitrogen oxide signals generated by the second nitrogen oxide sensor, and determining that the second nitrogen oxide values are within a second nitrogen oxide interval, and adapting the characteristic curve of the first nitrogen oxide sensor by the second nitrogen oxide values.

8 Claims, 1 Drawing Sheet

(51) Int. Cl.
*F01N 3/20* (2006.01)
*F01N 9/00* (2006.01)
*F01N 11/00* (2006.01)
*F02D 41/02* (2006.01)
*G01N 33/00* (2006.01)
*F02D 41/24* (2006.01)
*F01N 3/021* (2006.01)
*F01N 13/00* (2010.01)
*F01N 3/027* (2006.01)
*F01N 3/025* (2006.01)

(52) U.S. Cl.
CPC ............ *F01N 3/208* (2013.01); *F01N 3/2066* (2013.01); *F01N 9/00* (2013.01); *F01N 9/002* (2013.01); *F01N 11/00* (2013.01); *F01N 13/009* (2014.06); *F02D 41/029* (2013.01); *F02D 41/0275* (2013.01); *F02D 41/1463* (2013.01); *F02D 41/2441* (2013.01); *F02D 41/2474* (2013.01); *G01N 33/0037* (2013.01); *F01N 3/025* (2013.01); *F01N 3/027* (2013.01); *F01N 2560/021* (2013.01); *F01N 2560/026* (2013.01); *F01N 2610/02* (2013.01); *F01N 2900/0402* (2013.01); *F01N 2900/0416* (2013.01); *F01N 2900/0422* (2013.01); *F01N 2900/1402* (2013.01); *F01N 2900/16* (2013.01); *F01N 2900/1606* (2013.01); *F01N 2900/1616* (2013.01); *Y02A 50/245* (2018.01); *Y02T 10/24* (2013.01); *Y02T 10/47* (2013.01)

(58) Field of Classification Search
CPC ........ F01N 9/002; F01N 11/00; F01N 13/009; F01N 2560/021; F01N 2560/026; F01N 2610/02; F01N 2900/0402; F01N 2900/0416; F01N 2900/29; F01N 2900/0422; F01N 2900/1402; F01N 2900/16; F01N 2900/1606; F01N 2900/1616; F02D 41/0275; F02D 41/029; F02D 41/1461; F02D 41/1463; F02D 41/2441; F02D 41/2474; G01N 33/0037
See application file for complete search history.

(56) References Cited

FOREIGN PATENT DOCUMENTS

| | | |
|---|---|---|
| DE | 10 2008 039 687 | 3/2010 |
| DE | 10 2010 027984 | 10/2011 |
| DE | 11 2009 002 347 | 6/2013 |
| EP | 2 904 386 | 8/2015 |
| FR | 2 948 979 | 2/2011 |
| JP | 2015001206 | 1/2015 |
| WO | WO 2014/187516 | 11/2014 |

* cited by examiner

METHOD FOR ADAPTING THE CHARACTERISTIC CURVE OF THE NITROGEN OXIDE SENSOR IN AN INTERNAL COMBUSTION ENGINE

PRIORITY CLAIM

This is a U.S. national stage of application No. PCT/EP2017/052306, filed on Feb. 2, 2017. Priority is claimed on German Application No. DE102016204324.2, filed Mar. 16, 2016, the content of which is incorporated herein by reference.

BACKGROUND OF THE INVENTION

Field of the Invention

The present invention relates to a method for adapting a characteristic curve of a nitrogen oxide sensor in an internal combustion engine, in particular to a method for adapting the characteristic curve of a nitrogen oxide sensor, arranged upstream of an SCR catalytic converter, in an internal combustion engine with exhaust gas recirculation.

In internal combustion engines, in particular diesel internal combustion engines, it is known to use SCR (selective catalytic reduction) catalytic converters, which are used to reduce nitrogen oxides in the exhaust gases of the internal combustion engine. In this context, the chemical reaction at the SCR catalytic converter is selective, that is to say the nitrogen oxides (NO, $NO_2$) are preferably reduced while undesired secondary reactions, such as the oxidation of sulfur dioxide to form sulfur trioxide, are largely suppressed.

For the chemical reaction, urea is injected into the exhaust gas upstream of the SCR catalytic converter, which urea is subsequently at least partially decomposed into ammonia that can react with the exhaust gas to form water and nitrogen within the SCR catalytic converter. For example nitrogen oxide sensors and ammonia sensors are used to control the quantity of urea to be injected, in order to measure the respective portions in the exhaust section of the internal combustion engine and subsequently control the correct quantity of urea to be injected.

SUMMARY OF THE INVENTION

One aspect of the present invention is based on a method with which a deviation of a characteristic curve of a nitrogen oxide sensor can be reduced over the running time.

One aspect of the present invention is based on correcting the characteristic curve of a first nitrogen oxide sensor, arranged upstream of an SCR catalytic converter, of an internal combustion engine with exhaust gas recirculation by acquired nitrogen oxide values of a second nitrogen oxide sensor downstream of the SCR catalytic converter, when a particle filter arranged upstream of the SCR catalytic converter is in a regeneration phase. During the regeneration phase of the particle filter, the nitrogen oxide emission is usually reduced on the basis of the increased exhaust gas recirculation rate, wherein, in addition, the supply of urea is interrupted by a urea injection device arranged upstream of the SCR catalytic converter. In particular, at the increased exhaust gas temperature the ammonia formed by decomposition of the urea would be oxidized before it could react with the nitrogen oxides in the SCR catalytic converter.

According to one aspect of the present invention, a method for adapting the characteristic curve of a first nitrogen oxide sensor, arranged upstream of an SCR catalytic converter, of an internal combustion engine with exhaust gas recirculation is disclosed, which has the SCR catalytic converter, the first nitrogen oxide sensor arranged upstream of the SCR catalytic converter, a second nitrogen oxide sensor arranged downstream of the SCR catalytic converter, a particle filter arranged upstream of the SCR catalytic converter, and a urea injection device arranged upstream of the SCR catalytic converter. The method according to one aspect of the invention comprises determining that the particle filter is in a regeneration phase, increasing the exhaust gas recirculation rate during the regeneration phase of the particle filter, interrupting the supply of urea by the urea injection device during the regeneration phase of the particle filter, acquiring first nitrogen oxide values from first nitrogen oxide signals generated by the first nitrogen oxide sensor during the regeneration phase of the particle filter, and determining that the first nitrogen oxide values are within a first nitrogen oxide interval, acquiring second nitrogen oxide values from second nitrogen oxide signals generated by the second nitrogen oxide sensor during the regeration phase of the particle filter, and determining that the second nitrogen oxide values are within a second nitrogen oxide interval, and adapting the characteristic curve of the first nitrogen oxide sensor by the second nitrogen oxide values.

By determining that the first nitrogen oxide values are within a first nitrogen oxide interval and by determining that the second night nitrogen oxide values are within a second nitrogen oxide interval, it is checked whether the respective nitrogen oxide values acquired from the respective signals of the first and second nitrogen oxide sensors are essentially stable. Instead of the checking of the stability of the nitrogen oxide values, it is also possible to check the respective nitrogen oxide signals directly on the basis of the essentially linear profiles of the characteristic curves of the nitrogen oxide sensors, in order to determine whether said nitrogen oxide signals are within an interval and/or whether they are stable.

In one preferred refinement, the first nitrogen oxide interval describes an interval which extends about a first mean value, acquired from the first nitrogen oxide values, with ±10%, in particular ±5%. In addition, in this context, the second nitrogen oxide interval describes an interval which extends about a second mean value, acquired from the second nitrogen oxide values, with ±10%, in particular ±5%.

In a further preferred embodiment, the internal combustion engine has an ammonia sensor arranged downstream of the SCR catalytic converter. In this preferred refinement, the method also comprises generating an ammonia signal by the ammonia sensor, acquiring an ammonia value from the ammonia signals generated by the ammonia sensor, and determining that the acquired ammonia value is lower than a predetermined ammonia threshold value. The adaptation of the characteristic curve of the first nitrogen oxide sensor according to the present method is carried out only if it is determined that the acquired ammonia value is less than the predetermined ammonia threshold value. On the other hand, this means that when it is determined that the acquired ammonia value is higher than the predetermined ammonia threshold value, the adaptation of the characteristic curve according to the present invention cannot be carried out.

According to one preferred refinement, the predetermined ammonia threshold value is approximately 5 ppm, in particular approximately 1 ppm.

According to a further advantageous refinement, the method according to one aspect of the invention also comprises acquiring an absolute change gradient of the ammonia signals, and determining that the absolute change gradient of the ammonia signals is below a predetermined ammonia change threshold value. Within the scope of the present disclosure, an absolute change gradient describes a change over time in the signals that are detected in brief succession within a predetermined time interval. In particular, the change gradient can be an indication of stable values and/or signals.

When the characteristic curve of the first nitrogen oxide sensor is adapted, the delay between the signal of the first nitrogen oxide sensor and the signal of the second nitrogen oxide sensor is advantageously taken into account. The signals, characterizing an exhaust gas sample, between the first nitrogen oxide sensor and the second nitrogen oxide sensor are chronologically offset as a function of the flow behavior of the exhaust gas, for example the flow speed and/or flow path length between the first nitrogen oxide sensor and the second nitrogen oxide sensor. This chronological offset is preferably allowed for and taken into account in the adaptation.

According to a further aspect of the present invention, an exhaust section for an internal combustion engine with exhaust gas recirculation is disclosed, having an SCR catalytic converter, a particle filter arranged upstream of the SCR catalytic converter, in particular a diesel particle filter, a first nitrogen oxide sensor arranged upstream of the SCR catalytic converter and designed to generate a first nitrogen oxide signal that indicates the nitrogen oxide value upstream of the SCR catalytic converter, a urea injection device arranged upstream of the SCR catalytic converter and designed to inject a predetermined quantity of urea, a second nitrogen oxide sensor arranged downstream of the SCR catalytic converter and designed to generate a second nitrogen oxide signal that indicates the nitrogen oxide, an ammonia sensor arranged downstream of the SCR sensor and designed to generate an ammonia signal that indicates the ammonia value, and a control unit designed to receive the first nitrogen oxide signal, the second nitrogen oxide signal and the ammonia signal, and to execute a method according to the present disclosure.

BRIEF DESCRIPTION OF THE DRAWINGS

Further features and objects of the present invention are apparent to the person skilled in the art by considering the appended drawings, in which.

DETAILED DESCRIPTION OF THE PRESENTLY PREFERRED EMBODIMENTS

Figure 1:
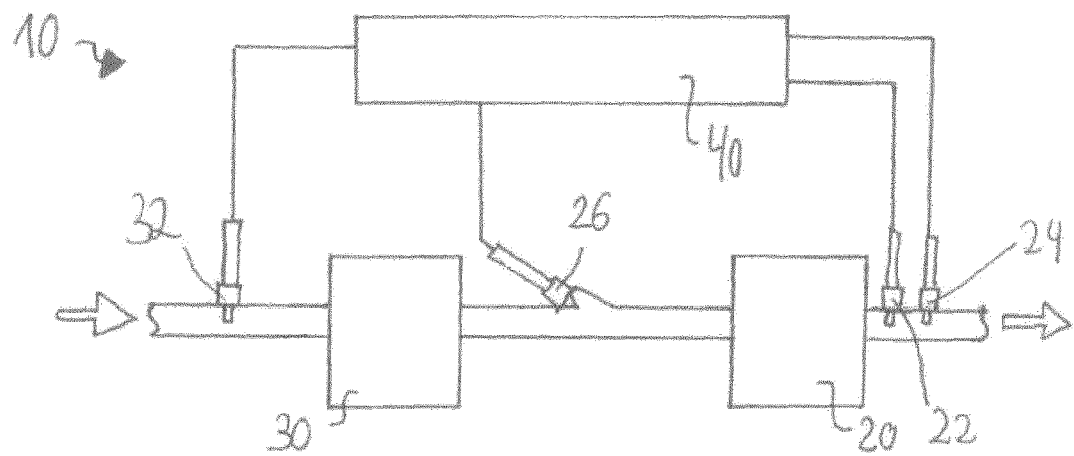
FIG. 1 is part of an exhaust section, disclosed by way of example, of an internal combustion engine with exhaust gas recirculation.

FIG. 1 shows a schematic view of part of an exhaust section 10 of an internal combustion engine (not illustrated in more detail). The exhaust section 10 has an SCR catalytic converter 20 designed to carry out a chemical reaction so that the nitrogen oxides in the exhaust gas can be reduced. A particle filter 30, for example a diesel particle filter, is arranged upstream of the SCR catalytic converter 20. In one preferred refinement, the SCR catalytic converter 20 and the particle filter 30 are integrated in one component unit. A nitrogen oxide sensor 22 and an ammonia sensor 24, which are designed to generate corresponding signals, are arranged downstream of the SCR catalytic converter 20. In particular, the nitrogen oxide sensor is designed to generate a nitrogen oxide signal which indicates a nitrogen oxide value. In a similar way, the ammonia sensor 24 is designed to generate an ammonia signal that indicates an ammonia value.

A urea injection device 26 is arranged upstream of the SCR catalytic converter 20 and is designed to inject a predetermined quantity of urea at predetermined times. The urea solution is designed to be decomposed by the exhaust gas such that ammonia is at least partially produced, which ammonia can react chemically in the SCR catalytic converter 20 and can therefore reduce the nitrogen oxides in the exhaust gas.

According to the exemplary refinement of the exhaust section 10 illustrated in FIG. 1, a further nitrogen oxide sensor 32 is also provided upstream of the particle filter 20, which nitrogen oxide sensor 32 is designed to generate a further nitrogen oxide signal that indicates a nitrogen oxide value.

A control unit 40, which can be, for example, part of the control system of the internal combustion engine, is connected to the nitrogen oxide sensor 22, the ammonia sensor 24, the urea injection device 26, and the further nitrogen oxide sensor 32 and is designed to receive signals from these devices and/or transmit signals to these devices in order to control them.

Figure 2:
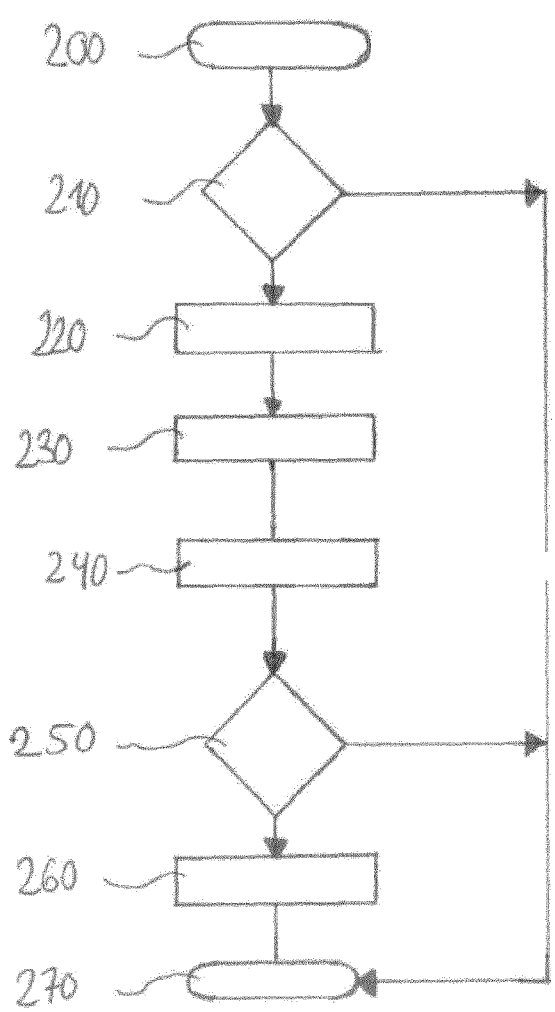
FIG. 2 is a flowchart of an exemplary method for adapting the characteristic curve of a nitrogen oxide sensor according to the present disclosure.

For example, the control system 40 is designed to execute a method according to FIG. 2. FIG. 2 shows an exemplary flowchart of a method for adapting the characteristic curve of a nitrogen oxide sensor of an internal combustion engine with exhaust gas recirculation.

The method starts at step 200, and it is determined at step 210 that the particle filter 30 is in a regeneration phase. A regeneration phase of the particle filter is necessary when the loading of the particle filter exceeds a predetermined threshold value, for example more than 90% of the maximum loading. If it is determined at step 210 that the particle filter 30 is not in a regeneration phase, the method proceeds to step 270 and ends there.

If it is determined at step 210 that the particle filter 30 is in a regeneration phase, the exhaust gas recirculation rate is increased at step 220. At the following step 230, the supply of urea by the urea injection device 26 is interrupted. In a subsequent step 240, first nitrogen oxide values are acquired from the first nitrogen oxide signals acquired by the first nitrogen oxide sensor 32. At the same time, at the step 240, second nitrogen oxide values are acquired from the second nitrogen oxide signals acquired by the second nitrogen oxide sensor 22.

At a subsequent step 250, it is checked whether the first and second nitrogen oxide values are within a first nitrogen oxide interval or within a second nitrogen oxide interval. That is to say it is determined whether the first and second nitrogen oxide signals are essentially stable. If it is determined at step 250 that the first nitrogen oxide signals are not within the first nitrogen oxide interval and/or the second nitrogen oxide signals are not within the second nitrogen oxide interval, the method proceeds to step 270 at which it is ended.

However, if it is determined at step 250 that both the first nitrogen oxide signals are within the first nitrogen oxide interval and the second nitrogen oxide signals are within the second nitrogen oxide interval, at step 260 the characteristic curve of the first nitrogen oxide sensor 32 is adapted by the nitrogen oxide values of the second nitrogen oxide sensor 22.

The method according to FIG. 2 can be expanded to the effect that an ammonia value is acquired from the ammonia signal generated by the ammonia sensor 24. It can then be determined whether the acquired ammonia value is lower than a predetermined ammonia threshold value, for example is approximately 5 ppm, in particular approximately 1 ppm.

In particular, it is advantageous to perform the adaptation at step 260 only when it is determined that the acquired quantity of ammonia is less than the predetermined ammonia threshold value. This means, conversely, that such adaptation does not take place if the ammonia value is higher than the predetermined ammonia threshold value.

In a similar way, the adaptation of the characteristic curve of the first nitrogen oxide sensor 32, which is presented above, is eliminated if it is determined that an absolute change gradient of the ammonia signals of the ammonia sensor exceeds a predetermined ammonia change threshold value in addition to or as an alternative to the exceeding of the ammonia threshold value.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for adapting a characteristic curve of a first nitrogen oxide sensor of an internal combustion engine with exhaust gas recirculation, the first nitrogen oxide sensor arranged upstream of an SCR catalytic converter, a second nitrogen oxide sensor arranged downstream of the SCR catalytic converter, a particle filter arranged upstream of the SCR catalytic converter, and a urea injection device arranged upstream of the SCR catalytic converter, wherein the method comprises:
determining that the particle filter is in a regeneration phase;
increasing an exhaust gas recirculation rate during the regeneration phase of the particle filter;
interrupting a supply of urea by the urea injection device during the regeneration phase of the particle filter;
acquiring first nitrogen oxide values from first nitrogen oxide signals generated by the first nitrogen oxide sensor during the regeneration phase of the particle filter;
determining that the first nitrogen oxide values are within a first nitrogen oxide interval;
acquiring second nitrogen oxide values from second nitrogen oxide signals generated by the second nitrogen oxide sensor during the regeneration phase of the particle filter;
determining that the second nitrogen oxide values are within a second nitrogen oxide interval; and
adapting the characteristic curve of the first nitrogen oxide sensor based at least in part on the second nitrogen oxide values.

2. The method as claimed in claim 1, wherein
the first nitrogen oxide interval describes an interval that extends about a first mean value, acquired from the first nitrogen oxide values, with ±10%, and
the second nitrogen oxide interval describes an interval that extends about a second mean value, acquired from the second nitrogen oxide values, with ±10%.

3. The method as claimed in claim 1, wherein there is a predetermined time difference between generation of the first nitrogen oxide signals by the first nitrogen oxide sensor and generation of the second nitrogen oxide signals by the second nitrogen oxide sensor, and during the adaptation of the characteristic curve of the first nitrogen oxide sensor the predetermined time difference is taken into account in the second nitrogen oxide values.

4. The method as claimed in claim 1, wherein the internal combustion engine also has an ammonia sensor arranged downstream of the SCR catalytic converter, the method further comprising:
generating an ammonia signal by the ammonia sensor;
acquiring an ammonia value from the ammonia signal; and
determining that the acquired ammonia value is lower than a predetermined ammonia threshold value.

5. The method as claimed in claim 4, further comprising:
acquiring an absolute change gradient of ammonia signals; and
determining that the absolute change gradient of the ammonia signals is below a predetermined ammonia change threshold value.

6. The method as claimed in claim 4, wherein the predetermined ammonia threshold value is 5 ppm.

7. The method as claimed in claim 6, wherein the predetermined ammonia threshold value is 1 ppm.

8. An exhaust section for an internal combustion engine with exhaust gas recirculation, comprising:
an SCR catalytic converter;
a particle filter arranged upstream of the SCR catalytic converter;
a first nitrogen oxide sensor arranged upstream of the SCR catalytic converter and configured to generate a first nitrogen oxide signal that indicates a nitrogen oxide value upstream of the SCR catalytic converter;
a urea injection device is arranged upstream of the SCR catalytic converter and configured to inject a predetermined quantity of urea;
a second nitrogen oxide sensor arranged downstream of the SCR catalytic converter and configured to generate a second nitrogen oxide signal that indicates a nitrogen oxide value downstream of the SCR catalytic converter;
an ammonia sensor arranged downstream of the SCR catalytic converter and configured to generate an ammonia signal that indicates an ammonia value downstream of the SCR catalytic converter; and
a control unit configured to receive at least the first nitrogen oxide signal, the second nitrogen oxide signal, and the ammonia signal and based on inputs:
determine that the particle filter is in a regeneration phase;
increase an exhaust gas recirculation rate during the regeneration phase of the particle filter;
interrupt a supply of urea by the urea injection device during the regeneration phase of the particle filter;

acquire first nitrogen oxide values from first nitrogen oxide signals generated by the first nitrogen oxide sensor during the regeneration phase of the particle filter;
determine that the first nitrogen oxide values are within a first nitrogen oxide interval;
acquire second nitrogen oxide values from second nitrogen oxide signals generated by the second nitrogen oxide sensor during the regeneration phase of the particle filter;
determine that the second nitrogen oxide values are within a second nitrogen oxide interval; and
adapt a characteristic curve of the first nitrogen oxide sensor based at least in part on the second nitrogen oxide values.

* * * * *